United States Patent
McAteer et al.

(10) Patent No.: US 11,176,325 B2
(45) Date of Patent: *Nov. 16, 2021

(54) ADAPTIVE EVALUATION OF META-RELATIONSHIPS IN SEMANTIC GRAPHS

(71) Applicant: INTERNATIONAL BUSINESS MACHINES CORPORATION, Armonk, NY (US)

(72) Inventors: Seamus R. McAteer, Navan (IE); Daniel McCloskey, Santry (IE); Aditya Mohan, Ongar (IE); Mikhail Sogrin, Kildalkey (IE)

(73) Assignee: International Business Machines Corporation, Armonk, NY (US)

( * ) Notice: Subject to any disclaimer, the term of this patent is extended or adjusted under 35 U.S.C. 154(b) by 779 days.

This patent is subject to a terminal disclaimer.

(21) Appl. No.: 15/632,564

(22) Filed: Jun. 26, 2017

(65) Prior Publication Data

US 2018/0373699 A1    Dec. 27, 2018

(51) Int. Cl.
*G06F 40/30*    (2020.01)
*G06F 16/901*    (2019.01)
(Continued)

(52) U.S. Cl.
CPC .......... *G06F 40/30* (2020.01); *G06F 16/3338* (2019.01); *G06F 16/9024* (2019.01);
(Continued)

(58) Field of Classification Search
CPC .. G06F 40/30; G06F 16/3338; G06F 16/9024; G06F 16/907; G06N 5/022; G06N 5/045; G16H 10/20

See application file for complete search history.

(56) References Cited

U.S. PATENT DOCUMENTS 8,930,178 B2   1/2015  Pestian et al.
9,336,306 B2   5/2016  McAteer et al.
(Continued)

FOREIGN PATENT DOCUMENTS

CN   101630314 B   12/2011
CN   106339401 A    1/2017
(Continued)

OTHER PUBLICATIONS

Cambria et al., "SenticNet 2: A Semantic and Affective Resource for Opinion Mining and Sentiment Analysis," in Proc. 25th Int'l Fla. Artificial Intelligence Res. Soc. Conf. 202-07 (2012). (Year: 2012).*

(Continued)

*Primary Examiner* — Kamran Afshar
*Assistant Examiner* — Ryan C Vaughn
(74) *Attorney, Agent, or Firm* — Dmitry Paskalov

(57) ABSTRACT

A method and system are provided for adaptive evaluation of meta-relationships in semantic graphs. The method includes providing a semantic graph based on a knowledge base in which concepts in the form of graph nodes are linked by semantic relationships in the form of graph edges. Metadata are encoded in the edges and nodes of the semantic graph, of weightings for measuring a meta-relationship, wherein the meta-relationship applies to the concepts of the semantic graph and is independent of the semantic relationship defined by the edges of the semantic graph. A graph activation is carried out for an input context relating to one or more concepts of the semantic graph, wherein the weightings are applied to a spreading activation signal through the semantic graph to produce a measure of the meta-relationship for a sub-set of concepts of the semantic graph.

11 Claims, 9 Drawing Sheets

(51) Int. Cl.
  G06N 5/02     (2006.01)
  G06F 16/33    (2019.01)
  G06F 16/907   (2019.01)
  G06N 5/04     (2006.01)
  G16H 10/20    (2018.01)

(52) U.S. Cl.
  CPC .......... *G06N 5/022* (2013.01); *G06F 16/907* (2019.01); *G06N 5/045* (2013.01); *G16H 10/20* (2018.01)

(56) References Cited

U.S. PATENT DOCUMENTS

| | | | |
|---|---|---|---|
| 9,659,004 | B2 | 5/2017 | Okura |
| 10,002,371 | B1 | 6/2018 | Baker |
| 2002/0091736 | A1* | 7/2002 | Wall ................ G06F 16/958 715/234 |
| 2005/0010553 | A1* | 1/2005 | Liu .................. G06F 16/58 |
| 2013/0155068 | A1 | 6/2013 | Bier et al. |
| 2015/0120623 | A1 | 4/2015 | Morara |
| 2015/0261743 | A1* | 9/2015 | Sengupta ........... G06F 40/289 704/9 |
| 2016/0321357 | A1 | 11/2016 | Novacek |
| 2018/0373701 | A1 | 12/2018 | McAteer |

FOREIGN PATENT DOCUMENTS

| | | | |
|---|---|---|---|
| CN | 110692050 | A | 1/2020 |
| DE | 12018001876 | T5 | 12/2019 |
| GB | 2578065 | A | 2/2020 |
| JP | 2008310784 | A | 12/2008 |
| JP | 2015060243 | A | 3/2015 |
| JP | 2016212838 | A | 12/2016 |
| WO | 2019003069 | A1 | 1/2019 |

OTHER PUBLICATIONS

Shen et al., "LINDEN: Linking Named Entities with Knowledge Base via Semantic Knowledge," in Proc. 21st Int'l Conf. World Wide Web 449-58 (2012). (Year: 2012).*
Dehdarbehbahani et al., "Semi-Supervised Word Polarity Identification in Resource-Lean Languages," in 58 Neural Networks 50-59 (2014). (Year: 2014).*
Torres et al., "Similarity for Natural Semantic Networks," in Int'l Conf. Similarity Search and Applications 195-200 (2014). (Year: 2014).*
Barbosa et al., "Robust Sentiment Detection on Twitter from Biased and Noisy Data," Coling 2010: Poster Volume, pp. 36-44, Beijing, Aug. 2010 (Best Date Available), http://www.aclweb.org/anthology/C10-2005.
DeVitt et al., "Sentiment Polarity Identification in Financial News: A Cohesion-based Approach," Proceedings of the 45th Annual Meeting of the Association of Computational Linguistics, 2007 (Best Date Available), pp. 1-8.
Calais Guerra et al., "From Bias to Opinion: A Transfer-Learning Approach to Real-Time Sentiment Analysis," KDD '11, Aug. 21-24, 2011, San Diego, California, USA, Copyright ACM, https://pdfs.semanticscholar/org/ce4d/63fa44e0f2fcd1782c0005c516dbeab75c0d.pdf, pp. 150-158.
Higgins et al, "The Cochrane Collaboration's tool for assessing risk of bias in randomised trials", Published Oct. 18, 2011, Cite this as BMJ, http://www.bmj.com/content/343/bmj.d5928.long, Printed on Jun. 21, 2017, pp. 1-14.
IBM, "AlchemyLanguage," IBM Watson Developer Cloud, https://alchemy-language-demo.mybluemix.net/, Printed on Jun. 21, 2017, pp. 1-2.
Ingvaldsen et al., "Handling Shape Variations in Geographical Distance Rankings For Local News Recommendation," GIR '15, Nov. 26-27, 2015, Paris, France, Copyright 2015 ACM, http://dl.acm.org/citation.cfm?id=2837702, pp. 1-2.
Iqbal et al., "Bias-Aware Lexicon-Based Sentiment Analysis," SAC '15, Apr. 13-17, 2015, Salamanca, Spain, Copyright 2015, ACM, http://web.lums.edu.pk/~akarim/pub/bias_aware_lexicon_based_sac2015.pdf, pp. 845-850.
Jonnagaddala et al., "Coronary artery disease risk assessment from unstructured electronic health records using text mining," Journal of Biomedical Informatics 58 (2015), http://www.sciencedirect.com/science/article/pii/S1532046415001707, pp. S203-S210, Available online Aug. 28, 2015.
MAC an tSAOIR, "Using Spreading Activiation to Evaluate and Improve Ontologies," Proceedings of COLING 2014, the 25th International Conference on Computational Linguistics, pp. 2237-2248, Aug. 23-29, 2014, Dublin, Ireland.
Montejo-Raez et al., "Ranked WordNet Graph for Sentiment Polarity Classification in Twitter," Article in Computer Speech & Language 28(1), Jan. 2013, DOI: 10.1016/j.csl.2013.04.001, pp. 1-16.
Pandita et al., "WHYPER: Towards Automating Risk Assessment of Mobile Applications," Proceedings of the 22nd USENIX Security Symposium, Aug. 14-16, 2013, Washington, D.C., USA, pp. 527-542.
Recasens et al., "Linguistic Models for Analyzing and Detecting Biased Language," https://www.cs.cornell.edu/%7Ecristian/Biased_language_files/neutrality.pdf, Proceedings of the 51st Annual Meeting of the Association for Computational Linguistics, pp. 1-10, Sofia, Bulgaria, Aug. 4-9, 2013.
SentiStrength, "SentiStrength Frequently Asked Questions," http://sentistrength.wlv.ac.uk/faq.html, Printed on Jun. 21, 2017, pp. 1-3.
SentiStrength, "SentiStrength," http://sentistrength.wlv.ac.uk/, Printed on Jun. 21, 2017, pp. 1-10.
Wadbude et al., "User Bias Removal in Review Score Prediction," May 12, 2017, https://arxiv.org/pdf/1612.06821.pdf, arXiv:1612.06821v2 [cs.CL], pp. 1-6.
Wang et al., "Identify Online Store Review Spammers via Social Review Graph," ACM Transactions on Intelligent Systems and Technology, vol. 3, No. 4, Article 61, Publication Date: Sep. 2012, pp. 61:1-61:21.
Cambria et al., "Sentic Activation: A Two-Level Affective Common Sense Reasoning Framework", Proceedings of the Twenty-Sixth AAAI Conference on Artificial Intelligence, Toronto, Ontario, Canada, Jul. 22-26, 2012, Copyright 2012, Association for the Advancement of Artificial Intelligence, www.aaai.org, pp. 186-192.
IBM, "Tone Analyzer", IBM Watson Developer Cloud, https://tone-analyzer-demo.mybluemix.net/?cm_mc_uid=450969397849, printed on Jun. 22, 2017, 1 page.
Lexalytics, "Semantria API Lexalytics' Text and Sentiment Analysis, in the cloud", https://www.lexalytics.com/semantria, printed on Jun. 22, 2017, pp. 1-6.
Mell et al., "The NIST Definition of Cloud Computing," U.S. Department of Commerce, National Institute of Standards and Technology, Sep. 2011, p. 1-7, Special Publication 800-145.
Socher et al., "Recursive Deep Models for Semantic Compositionality Over a Sentiment Treebank", Proceedings of the 2013 Conference on Empirical Methods in Natural Language Processing, pp. 1631-1642, Seattle, Washington, USA, Oct. 18-21, 2013, copyright 2013 Association for Computational Linguistics.
Wu et al., "Structural opinion mining for graph-based sentiment representation", Proceedings of the 2011 Conference on Empirical Methods in Natural Language Processing, pp. 1332-1341, Edinburgh, Scotland, UK, Jul. 27-31, 2011, copyright 2011 Association for Computational Linguistics.
IBM: List of IBM Patents or Patent Applications Treated as Related (Appendix P), May 1, 2018, pp. 1-2.
International Search Report and Written Opinion of International Application No. PCT/IB2018/054610, dated Sep. 29, 2018.
Maas et al., "Learning Word Vectors for Sentiment Analysis," Proceedings of the 49th Annual Meeting of the Association for Computational Linguistics, Jun. 19-24, 2011, pp. 142-150.
McAteer et al.., "Adaptive Evaluation of Meta-Relationships in Semantic Graphs," Application and Drawings, Filed on Jun. 22, 208, 40 Pages, Japanese Patent Application No. 2019-569743.
Mishra et al., "Question Classification using Semantic, Syntactic and Lexical Features," International Journal of Web & Semantic Technology (IJWesT), vol. 4, No. 3, Jul. 2013, pp. 39-47.

(56) References Cited

OTHER PUBLICATIONS

Japanese Notice of Reasons for Refusal of Japanese Application No. 2019-569743, dated Jul. 6, 2021, 12 pages.

\* cited by examiner

ADAPTIVE EVALUATION OF META-RELATIONSHIPS IN SEMANTIC GRAPHS

BACKGROUND

The present invention relates to semantic graphs, and more specifically, to adaptive evaluation of meta-relationships in semantic graphs.

Graphs of semantic concepts and relationships derived from structured knowledge are an extremely valuable resource for high-precision natural language processing (NLP) systems.

An ontology, in computer science, is defined as an "explicit specification of a shared conceptualization", where a conceptualization may be some subset of real-world semantics, with respect to the requirements for a given task. It can contain concepts or classes of object, object properties, and inter-concept relationships, as well as instances of these in the target domain. Such structured resources facilitate the sharing and re-use of domain knowledge, and are invaluable for NLP applications. A primary example of such a resource is the Unified Medical Language System (UMLS), provided by the National Library of Medicine (NLM, 2013). The data set consists of a large lexicon, including millions of instance surface forms, in conjunction with an ontology of concepts and inter-concept relationships in the medical domain.

The theory of spreading activation was first proposed in an abstract model of human semantic memory, in order to artificially represent the means by which a human's brain might process and understand the semantics of natural language. This model was enhanced for retrieval tasks and provided inspiration for research in many other related fields, from cognitive psychology to neuroscience, to natural language processing, among others.

The basic premise of spreading activation is related to that of connectionism in artificial intelligence, which uses similar models for neural networks to reflect the fan-out effect of electrical signal in the human brain. In the case of neural networks, a vertex in the graph could represent a single neuron, and edges could represent synapses. In information retrieval and word-sense disambiguation, generally vertices will represent word-senses and edges will represent some form of relationship, either lexical or semantic linkage, between these senses.

A spreading activation strategy is described in the paper "Using Spreading Activation to Evaluate and Improve Ontologies" by Ronan Mac an tSaoir, Proceedings of COLING 2014, the 25$^{th}$ International Conference on Computational Linguistics: Technical Papers, pages 2237-2248, Dublin, Ireland, Aug. 23-29, 2014. This technique involves processing a document of text and activating nodes in the semantic graph as they are discovered, by propagating a signal from these nodes that then spreads through the graph, and accumulates potentially at other nodes which did not occur in the text.

There are various different implementations of this basic idea, but one implemented by IBM® Galaxy (IBM® and Galaxy are trademarks of International Business Machines Corporation) is useful for the purposes of word-sense disambiguation and word-sense inference.

There are various fields in NLP that analyze phenomena related to relationships between entities. Examples of such fields include: sentiment analysis, bias detection, geo-spatial inference, contextual relevance and risk assessment. Accurate scoring of such phenomena across entities is a need in the prior art methods and improved analysis of such phenomena is required.

SUMMARY

According to an aspect of the present invention there is provided a computer-implemented method for adaptive evaluation of meta-relationships in semantic graphs, comprising: providing a semantic graph based on a knowledge base in which concepts in the form of graph nodes are linked by semantic relationships in the form of graph edges; encoding in metadata of the edges and nodes of the semantic graph, weightings for measuring a meta-relationship, wherein the meta-relationship applies to the concepts of the semantic graph and is independent of the semantic relationship defined by the edges of the semantic graph; and carrying out a graph activation for an input context relating to one or more concepts of the semantic graph, wherein the weightings are applied to a spreading activation signal through the semantic graph to produce a measure of the meta-relationship for a sub-set of concepts of the semantic graph.

The described method provides the advantage of scoring a meta-relationship across concepts defined in a sub-set of a semantic graph using graph activation. The encoded weightings for the meta-relationship may be activated for concepts of an input context enabling complex scoring and analysis of the meta-relationship of interrelated entities.

Carrying out a graph activation for an input context may include: discovering instances of concepts in the input context and activating nodes corresponding to the concepts in the semantic graph, traversing a signal outward to adjacent nodes, activating these in turn whilst applying the weightings to the signal, and determining one or more focus nodes with the highest resultant activation signals. The method may output a resultant activated portion of the semantic graph reflecting the measurement of the meta-relationship in the input context. This provides an advantage of scoring the meta-relationship between instances of concepts of the input context.

The method may seed the graph with weightings for measures of a meta-relationship obtained from a set of resources independent of the knowledge base on which the semantic graph is based. This enables the weightings to be encoded for a particular application. The semantic graph may be used as a base to which measures of a meta-relationship may be superimposed.

The weightings may indicate multi-dimensional measurements for different aspects of the meta-relationship and/or polarities of the meta-relationship. A meta-relationship may have different aspects that may be measured and encoded as dimensions in the weightings. The weightings may also have polarities such that positive and negative values may be included.

In one embodiment, the weightings may be raw values that are obtained from the set of resources and may be updated in response to additions to the set of resources, wherein the raw values are applied during the graph activation.

In another embodiment, the weightings may be feature vectors that may be calculated in response to runtime inputs for the nodes for instances of concepts of an input context. This enables the advantage of runtime adaptation of the weightings based on the inputs for the input context being scored. The feature vectors may include relevance factors to be applied to the runtime inputs for the nodes and the relevance factors may be different for different nodes.

Additionally, the feature vectors may include semantic and/or lexical features for instances of concepts in the input context in addition to the meta-data relationship features. This enables the semantic relationships of the semantic graph to be incorporated into the analysis. Alternatively, the feature vectors may only relate to the meta-relationship.

The feature vectors may define confidence scores for the weightings and aggregation of meta-relationship measures using statistical techniques.

The meta-relationship may relate to a phenomenon in the form of one of the group of: sentiment analysis, bias evaluation, bias in predictive analysis, query expansion using information retrieval, risk assessment, geo-spatial inference, and suitability of treatment, use or handling including clinical trial matching. These phenomena may apply universally across the concepts of the semantic graph.

According to another aspect of the invention there is provided a system for adaptive evaluation of meta-relationships in semantic graphs, comprising: a processor and a memory configured to provide computer program instructions to the processor to execute the function of the components; a semantic graph component for providing a semantic graph based on a knowledge base in which concepts in the form of graph nodes are linked by semantic relationships in the form of graph edges; a meta-relationship component for encoding in metadata of the edges and nodes of the semantic graph, weightings for measuring a meta-relationship, wherein the meta-relationship applies to the concepts of the semantic graph and is independent of the semantic relationship defined by the edges of the semantic graph; and a runtime component for carrying out a graph activation for an input context relating to one or more concepts of the semantic graph, wherein the weightings are applied to a spreading activation signal through the semantic graph to produce a measure of the meta-relationship for a sub-set of concepts of the semantic graph.

The system may provide the advantage of enabling encoding of meta-relationship weightings that may be automatically applied to an input context provided a complex scoring of the meta-relationship for concepts of the input context.

The runtime component may include: a concept detection component for discovering instances of concepts in the input context; and a graph activation component for activating nodes corresponding to the concepts in the semantic graph, traversing a signal outward to adjacent nodes activating these in turn whilst applying the weightings to the signal, and determining one or more focus nodes with the highest resultant activation signals.

The system may include an output component for outputting a resultant activated portion of the semantic graph reflecting the measurement of the meta-relationship in the input context. The output component may include an ambient context component for outputting an activated sub-graph where the activation weightings on nodes and edges represent the measurement of the meta-relationship.

The system may include a weightings adding component for seeding the graph with weightings for measures of a meta-relationship obtained from a set of resources independent of the knowledge base on which the semantic graph is based. The system may further include a weighting updating component for updating the weightings in response to additions to the set of resources or input contexts.

The system may be incorporated into systems for measuring a meta-relationship that relates to a phenomenon in the form of one of the group of: sentiment analysis, bias evaluation, bias in predictive analysis, query expansion using information retrieval, risk assessment, geo-spatial inference, and suitability of treatment, use or handling including clinical trial matching.

According to a further aspect of the present invention there is provided a computer program product for adaptive evaluation of meta-relationships in semantic graphs, the computer program product comprising a computer readable storage medium having program instructions embodied therewith, the program instructions executable by a processor to cause the processor to: provide a semantic graph based on a knowledge base in which concepts in the form of graph nodes are linked by semantic relationships in the form of graph edges; encode in metadata of the edges and nodes of the semantic graph, weightings for measuring a meta-relationship, wherein the meta-relationship applies to the concepts of the semantic graph and is independent of the semantic relationship defined by the edges of the semantic graph; and carry out a graph activation for an input context relating to one or more concepts of the semantic graph, wherein the weightings are applied to a spreading activation signal through the semantic graph to produce a measure of the meta-relationship for a sub-set of concepts of the semantic graph.

BRIEF DESCRIPTION OF THE DRAWINGS

The subject matter regarded as the invention is particularly pointed out and distinctly claimed in the concluding portion of the specification. The invention, both as to organization and method of operation, together with objects, features, and advantages thereof, may best be understood by reference to the following detailed description when read with the accompanying drawings.

Preferred embodiments of the present invention will now be described, by way of example only, with reference to the following drawings in which.

Figure 1A:
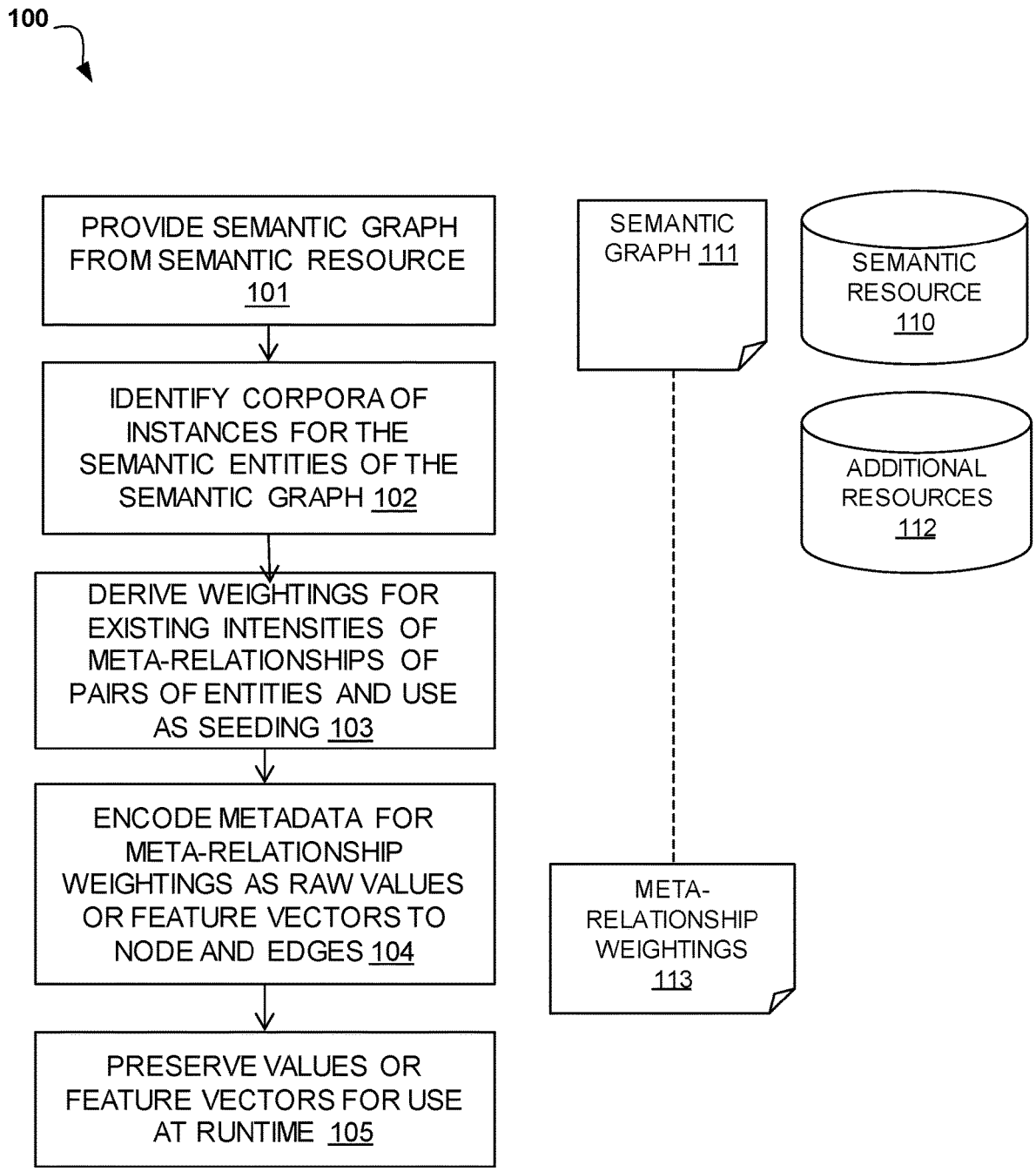
FIG. 1A is a flow diagram of an example embodiment of an aspect of a method in accordance with the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate,

DETAILED DESCRIPTION

The described method quantifies the intensity of a "meta-relationship" of a phenomenon between entities in a domain using spreading activation in a semantic graph, during natural language processing. The particulars of the meta-relationship and how the spreading signal should produce a measure of the intensity of this phenomenon is encoded in graph metadata, and changes according to the nature of the task and the domain in question.

The meta-relationship describes a phenomenon in the form of an attribute or characteristic applying universally to entities in the graph. The intensity of the phenomenon may be seeded in a semantic graph and adaptively measured using graph activation, such as spreading activation, when additional input resources are available.

This provides a technical solution to the problem of scoring a phenomenon across entities in an input context for a domain. The solution uses graph activation of a semantic graph that enables complex scoring and measurement between entities.

The term "meta-relationship" is used to describe a meta-level relationship or universal relationship that relates to a phenomenon that applies to the entities. The interpretation of "meta" is of a higher level and independent of the existing graph semantic relationships. The meta-relationship is superimposed on the existing semantics of any particular graph.

The meta-relationship is not part of the initial semantic graph and is not necessarily related to the relationship between entities represented by the edges in the graph. While a semantic graph might contain an edge for a semantic relevance such as "wrote" between two nodes or concepts, like "author" and "article", the described method is not focused on the nature or significance of this specific semantic relationship. Instead, it is leveraging this structure to quantify some higher-level meta context of a phenomenon, attribute or characteristic such as "sentiment", "bias", "geo-spatial relevance", or "risk exposure" that may apply overall or universally but with different intensities to the entities in the graph.

Traditional semantic graph terminology refers to graph nodes and edges for semantic relationships between concepts, which are the primary function of semantic graphs in natural language processing. The described method superimposes weightings of an additional aspect or phenomenon that may be measured. This additional phenomenon is not confined to the specifics of individual linked pairs of nodes.

A semantic graph is seeded with measures of intensity of the meta-relationships from contexts utilizing additional resources to those used to provide the initial semantic graph, in order to achieve an analysis of a subject of the meta-relationship during natural language processing.

Meta-relationships are exposed and assigned an intensity by processing the information stored in a graph. The extension to meta-relationships in addition to existing relationships in the semantic graph requires a second database of additional resources in addition to a first database of sources on which the semantic graph is based.

The default interpretation of a semantic graph is augmented by the described method with any number of various universal phenomena represented by the meta-relationships that fundamentally change how the same semantic graphs may be used in natural language processing. When users normally send a signal through any semantic graph, they expect the weights to tell them how closely related things are semantically. This is re-wired to represent whatever meta-relationship is preferred in context. This may be "how geographically close things are" or "how biased things are toward each other", etc.

Using spreading activation weight to quantify the strength of a semantic relationship between entities already exists. The described method extends this to quantify some phenomena other than simple context relevance by using the meta-relationship intensity.

A semantic graph may be customized at the node and edge level, whether through ascribing weight modifiers to specific node and edge types, or by modifying starting weights for specific nodes. The described method provides domain customized spreading activation of the graph structure and content in terms of higher-level contexts. Awareness of a meta-relationship of a phenomenon or context, such as corpus-relevance, bias or risk exposure has very different considerations and consequences for natural language processing.

There are many topics within the domain of natural language processing that focus on detecting the degree of intensity of a particular linguistic phenomenon or in quantifying a particular characteristic of some subject of analysis. The described method provides a technique that can be applied across many such tasks in order to produce ambient representations of the same quantities or phenomena. An ambient representation of a phenomenon such as bias or geographic relevance is essentially an activated sub-graph where the activation weights on nodes and edges represent the degree of intensity of the phenomenon. The word ambient here reflects the network or web-like structure of the representation.

Example embodiments in the following specific fields of natural language processing are described: sentiment analysis, bias detection, geo-spatial inference, contextual relevance, and risk assessment.

Referring to FIG. 1A, a flow diagram 100 shows an example embodiment of an aspect of the described method of applying meta-relationships for phenomena to semantic graphs for adaptive evaluation using graph activation.

A semantic graph 111 is provided 101, which may be built or may be an existing graph, for a semantic resource or resources 110 providing a knowledge base. Resources for this may be parse frames, ontologies, co-occurrence of named entity recognition (NER) data, etc. In this described method, the semantic graph 111 may be an existing pre-built graph, which may be used by the described method, in which case it is not necessary to revisit the original resources 110.

The method is not specific to any particular style of natural language text or domain terminology. The semantic graph used here can be derived from any natural language source upon which named entity recognition (NER) and natural language parsers can be applied.

The method may identify 102 corpora of instances in the form of additional resources 112 to be referenced for the phenomenon of interest. For a particular phenomenon for which the intensity is to be measured using the meta-relationships, examples in the form of additional resources 112 are used on which to base the initial metadata for graph activation. The additional resources 112 refer to the entities of the semantic graph 111 in the context of the phenomenon of interest.

The method may derive 103 weightings for meta-relationships of existing intensity and/or polarity between all pairs of entities that reflect the phenomenon that is the goal of the NLP task that may be used as seedings. This may be provided using prior analysis of the goal such as sentiment analysis or bias detection data, geographic distance data, IR statistics, risk factor scores, etc. The method leverages background knowledge to weight the semantic graph according to the task and domain.

The method may encode in metadata 104 meta-relationship weightings 113 as hardcoded raw values or as feature vectors. Node and edge weightings are a function of input data features, and may be stored as a raw value or as a feature vector for later calculation.

Metadata values or feature vectors for prior semantic graph implementations are normally a single positive value reflecting the accumulation of spreading signal at nodes or edges in the graph. In the described method, the weightings provided have a new meaning relating to the meta-relationship being evaluated.

A feature vector is an n-dimensional vector of numerical features that represent some object. Feature vectors are equivalent to the vectors of explanatory variables used in statistical procedures. Feature vectors are often combined with weightings using a dot product in order to construct a linear predictor function that is used to determine a score for making a prediction.

Feature vectors may include, but are not limited to, the following:
  i. semantic and lexical features of instances of the concept in the corpus;
  ii. intensity of the meta-relationship that is the primary goal of the task; this can also be multi-dimensional, for example, as in the case of bias or sentiment which can be polarized;
  iii. confidence scores for all of the above; and
  iv. aggregations of relevance and intensity measures using statistical techniques such as logistic regression on the same vector.

The intensity of the meta-relationship in the feature vectors may use runtime inputs for the nodes that may be combined with hardcoded relevance factors. These may be different for each node or type of node.

Relationships in the sense of physical links between nodes are not modified. Instead, the meta-relationship is reflected in the numeric value of the activation weighting and the sign of the value (+/−). A label of the meta-relationship (such as bias or risk exposure) is not encoded within the graph in nodes or edges. The change is that the signal intensity following spreading activation has a new meaning.

By preserving 105 the raw values or feature vectors for use at runtime, the method also facilitates the optional adaptation of graph weightings according to the nature of future inputs to the system.

The method does not require significant adaptation regardless of intent, whether it be sentiment analysis, opinion bias detection, geo-spatial relevance, semantic relevance, risk exposure, etc.

Figure 1B:
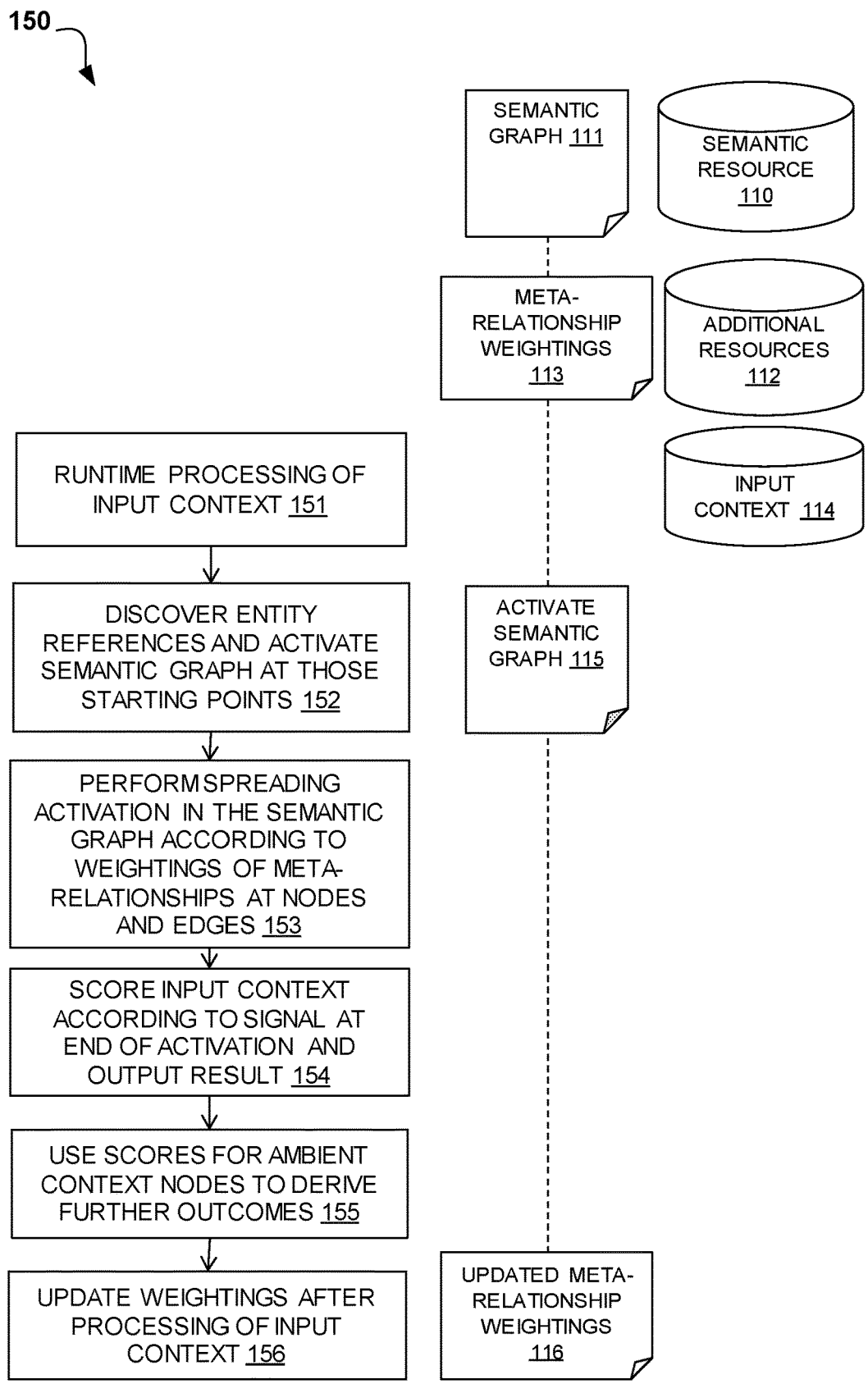
FIG. 1B is a flow diagram of an example embodiment of a further aspect of a method in accordance with the present invention.

Referring to FIG. 1B, a flow diagram 150 shows an example embodiment of another aspect of the described method of adaptive evaluation of meta-relationships for phenomena using graph activation.

When unseen text in the form of an input context 114 is processed 151 at runtime, the method may discover 152 entity references and activate the semantic graph 115 at those starting points. Typically, this may use the same NER generators used when building 101 the semantic graph.

The method may perform 153 spreading activation in the semantic graph by propagating the signal according to the weightings of the meta-relationship at nodes and edges that were added in the method of FIG. 1A.

By discovering instances of concepts in an input context 114, using the set of unique identifiers for instances, corresponding nodes can be activated in the semantic graph, from where a signal traverses outward across adjacent nodes, activating these in turn.

In one embodiment, the discovered instances of concepts in an input context may activate the corresponding nodes using hardcoded raw values of weightings of the nodes. In another embodiment, inputs from the instances of concepts may be used for calculating feature vectors for the nodes. The inputs may be combined with hardcoded relevance factors that may vary for different nodes or types of nodes as defined in the weighting feature vectors.

As the signal spreads farther from a source node, it gets weaker by an amount specified in an associated weighting model for nodes and edges in the graph. If the signal spreads from multiple nearby source nodes, the signal will combine, and points of overlap will be activated to a greater degree. The nodes that accumulate the most activation are deemed to be the focus nodes for the input context. The resulting activated portion of the graph will reflect the inherent intensity of the phenomenon of the meta-relationships in the input context.

The input context 114 may be scored 154 by detected entities according to the intensity of the signal at the end of activation and this score may be output as a result.

The scores may be used 155 for ambient context nodes in order to derive further outcomes in the same context, which may be output as a further result.

The described method is not dependent on explicit occurrences of entities in the context being analyzed; the association and scoring of additional external concepts is possible via ambient connectivity in the graph. The method allows ambient context of indirectly related entities to affect the assessment of intensity for relationships in a particular context giving a much more comprehensive view.

The method facilitates detailed entity level relationships, and scores of relationship intensity between pairs of entities, rather than simple aggregated "gist" scores for whole contexts.

In several embodiments, it may be helpful to update 156 the meta-relationship weightings 116 according to how the signals have changed after the input context 114 has been processed. This may use the method of deriving 103 the weightings as used in FIG. 1A. For example, historic bias between the author and an unlisted topic may now be different as a result of activation using the input context 114.

Figure 2:
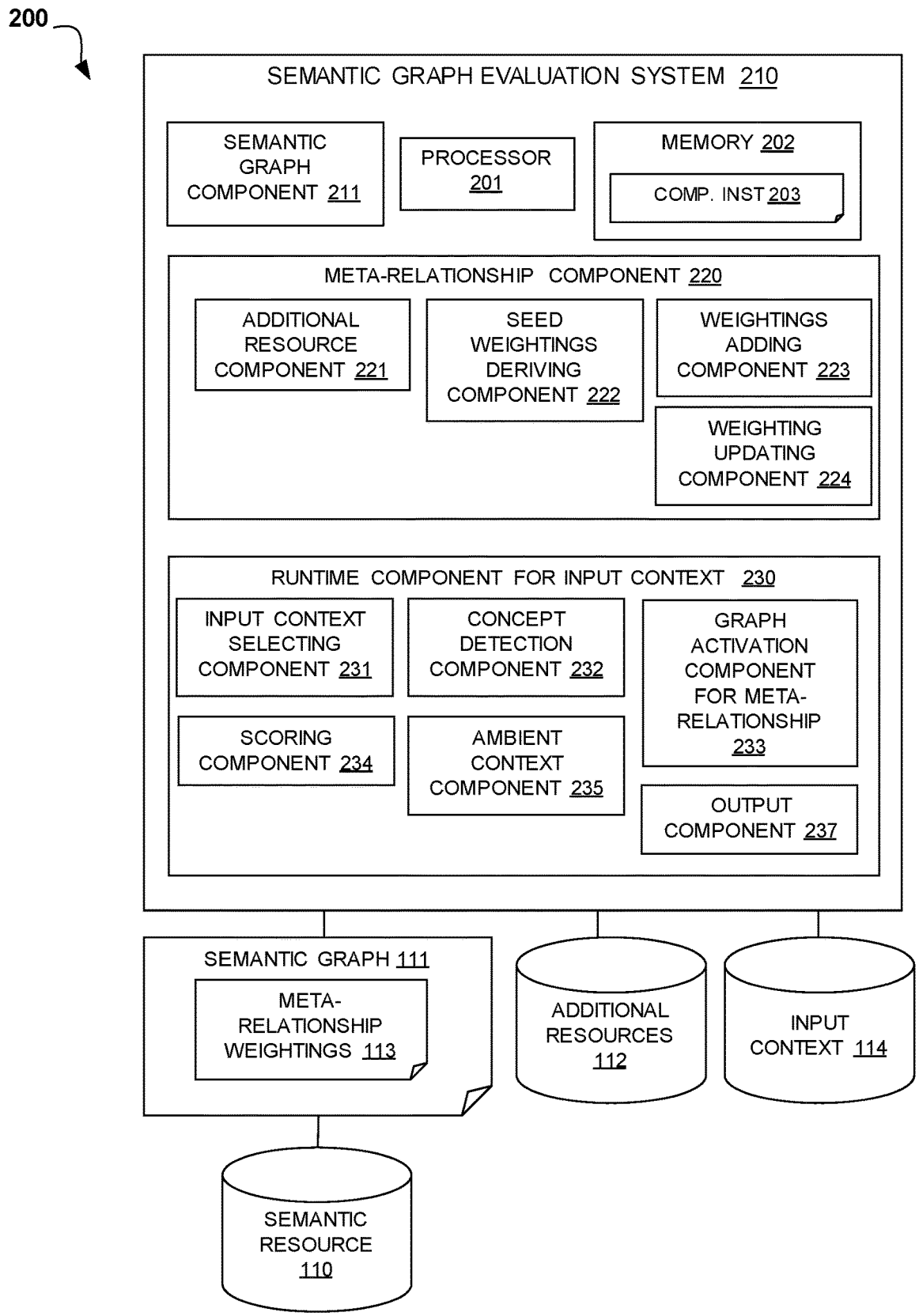
FIG. 2 is block diagram of an example embodiment of a system in accordance with the present invention.

Referring to FIG. 2, a block diagram shows a system 200 as an example embodiment of the described system in the form of a semantic graph evaluation system 210.

The semantic graph evaluation system 210 includes at least one processor 201, a hardware module, or a circuit for executing the functions of the described components which may be software units executing on the at least one processor. Multiple processors running parallel processing threads may be provided enabling parallel processing of some or all of the functions of the components. Memory 202 may be configured to provide computer instructions 203 to the at least one processor 201 to carry out the functionality of the components.

The semantic graph evaluation system 210 may be provided as part of a semantic graph creation system (not shown) or as an independent system for adaptive evaluation of meta-relationships in sematic graphs by adding meta-relationship weightings 113 for a phenomenon to be evaluated ta a semantic graph 111 based on semantic resources 110. The semantic graph evaluation system 210 may use additional resources 112 relating to the phenomenon being evaluated for seeding weighting values for the meta-relationship. Input contexts 114 may be provided at runtime for evaluation of the phenomenon using graph activation.

The semantic graph evaluation system 210 may include a semantic graph component 211 for providing a semantic graph based on semantic resources 110 forming a knowledge base in which concepts in the form of graph nodes are linked by semantic relationships in the form of graph edges.

The semantic graph evaluation system 210 may include a meta-relationship component 220 for encoding in metadata of the edges and nodes of the semantic graph 111, weightings for intensities of a meta-relationship. The meta-relationship may apply to the concepts of the semantic graph 111 and may be independent of the semantic relationship defined by the edges of the semantic graph.

The meta-relationship component 220 may include an additional resource component 221 for selecting additional resources 112 on which the meta-relationship weightings may be based. The meta-relationship component 220 may also include a seed weightings deriving component 222 for deriving seed weightings to be used for the meta-relationship derived from the additional resources 112. The meta-relationship component 220 may also include a weightings adding component 223 for seeding the semantic graph with weightings for intensities of a meta-relationship obtained from the set of additional resources 112 independent of the knowledge base on which the semantic graph 111 is based.

The meta-relationship component 220 may include a weighting updating component 224 for updating the weightings in response to additions to the additional resources 112 or input contexts 114.

The semantic graph evaluation system 210 may include a runtime component 230 for carrying out a graph activation for an input context 114 relating to one or more concepts of the semantic graph. The weightings may be applied to a spreading activation signal through the semantic graph 111 to produce a measure of intensity of the meta-relationship for a sub-set of concepts of the semantic graph.

The runtime component 230 may include an input context selecting component 231 for selecting an input context 114 to be evaluated. The runtime component 230 may include a concept detection component 232 for discovering instances of concepts in the input context 114.

The runtime component 230 may include a graph activation component for a meta-relationship 233 for activating nodes corresponding to the concepts in the semantic graph 111, traversing a signal outward to adjacent nodes activating these in turn whilst applying the weightings to the signal, and determining one or more focus nodes with the highest resultant activation signals.

The runtime component 230 may include a scoring component 234 for scoring nodes in response to the graph activation and an ambient context component 235 for an activated sub-graph where the activation weightings on nodes and edges represent the degree of intensity of the meta-relationship.

The runtime component 230 may include an output component 237 for outputting a resultant activated portion of the semantic graph reflecting the intensity of the meta-relationship in the input context.

Various examples of different phenomena for which meta-relationships are evaluated are described in the following sections.

Clinical Trial Matching

In an example embodiment, a semantic graph may be built or an existing graph used from Unified Medical Language System (UMLS) data for medical domain concepts, such as: "Tumours", "Progesterone" or "Lymph nodes", etc.

In conjunction with this semantic graph, a corpus of annotated patient records of successful trial candidates may be used to configure the weightings of the graph activation for this task. Alternatively, a set of hardcoded values or value ranges for acceptance criteria in the trial, sourced from medical experts, may be used in a similar fashion.

Node weightings may be configured for the relevance of the node to the clinical trial as feature vectors. The feature vectors take as inputs a particular patient's input to the nodes.

In this example, the final score encodes the degree to which a patient matches the requirements for a clinical trial. Nodes and edges in the graph may be medical domain concepts such as: "Tumours" or "Progesterone" or "Lymph nodes", etc. Each of these concepts may have a different relevance depending on the drug being tested, and the intensity of the match is a function of this prior hardcoded relevance along with the value that the evaluated patient is showing for this concept.

So, the feature vector may be different for every node. The following are some examples:
  a) A "TumourSize" node has a hardcoded relevance factor of 0.9, so when a patient comes in and has associated value for this concept, the vector may contain the normalized value of (patient tumour size*0.9);
  b) If the "ProgesteroneLevel" node has a relevance of 0.8 for this drug, the vector contains (patient's progesterone level*0.8);
  c) The node for "ki67 proliferation index" may have a normalized percentage (n %*0.7).

A patient's available values are then used to activate the graph, using default values for characteristics that are not available, and the net accumulation of signal on each of the important concepts reflects the general suitability of the trial, for this patient.

Sentiment Analysis

Sentiment analysis involves the extraction of subjective opinion and categorizing it as positive, negative or neutral, or extending this capability to provide some numerical representation. Typically, sentiment analysis is applied at a document level, and the aggregated polarity of the document is applied to the topic of discussion. Increasingly, phrase level sentiment detection is applied to particular elements of the topic, known as "aspect level sentiment analysis". In this case, a separate score is aggregated in the document or corpus, for each sub-element of the overall topic. One of the most difficult parts of this process is recognizing when the inherent sentiment of a word changes in context, such as in the phrases "negative test result" versus "negative experience".

Sentiment analysis is an example of a phenomenon for which meta-relationships may be applied and evaluated using a semantic graph using the described method.

Example of Sentiment Analysis Evaluation:

In an example embodiment, a semantic graph may be built or an existing graph used from Unified Medical Language System (UMLS) ontology data.

Additional medical documents may be used as the additional resources relating to the sentiment to be analyzed. The medical documents may be annotated with the same concepts of the semantic graph. Named entity phrases may be associated with sentiment phrases, such as "strongly increased", that have inherent sentiment polarity in different contexts. For each document in the corpus or additional resources, node weightings are configured for the sentiments using raw values or vectors.

Figure 3:
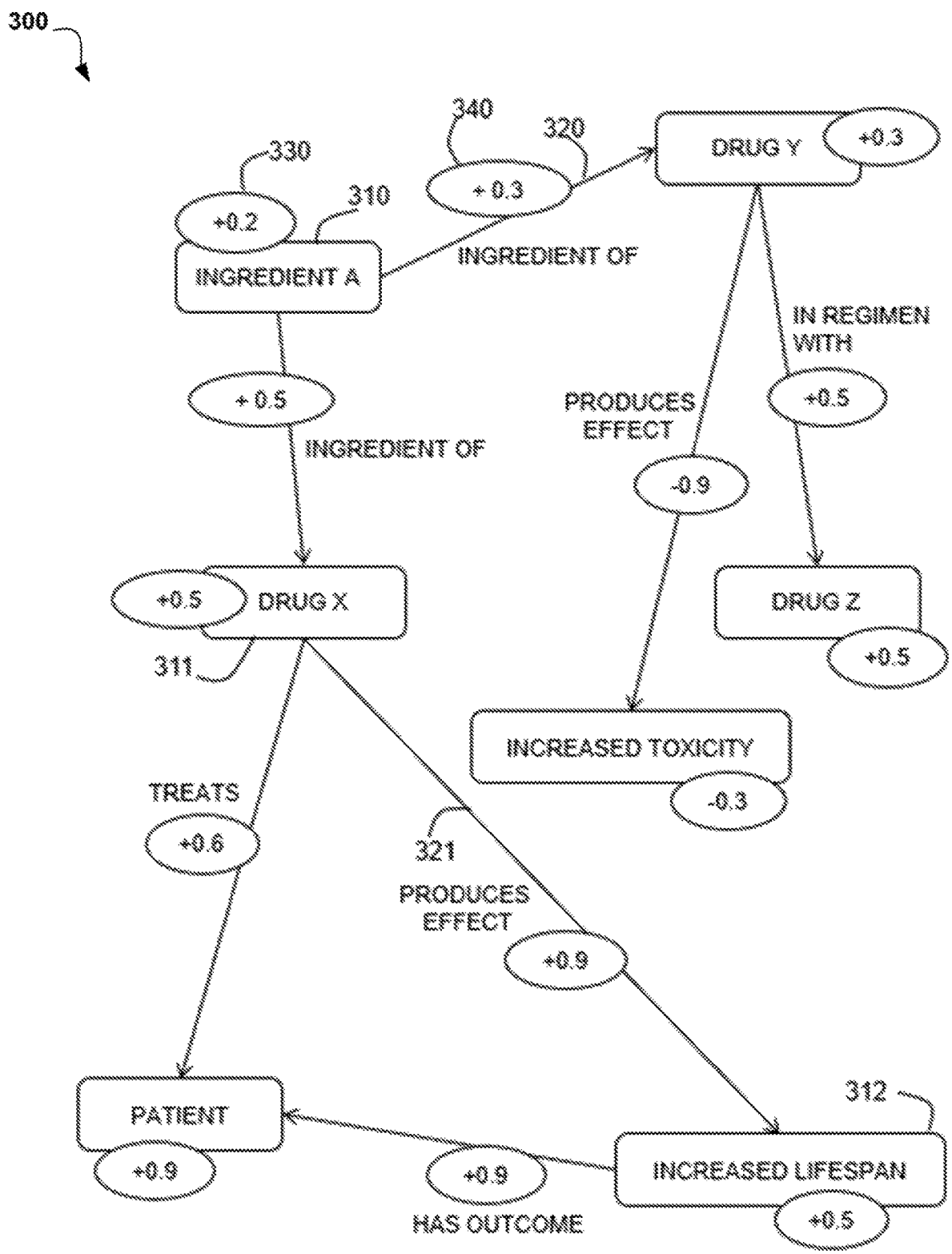
FIG. 3 is a schematic diagram illustrating a first example embodiment of a method in accordance with the present invention.

FIG. 3 is a schematic diagram of an extract 300 from a semantic graph that illustrates meta-relationship weightings of sentiment analysis. The semantic graph extract 300 shows nodes 310 relating to concepts of the UMLS with edges 320 relating to semantic relationships between the nodes 310. For example, node 311 of "Drug X" has the relationship 321 of "produces effect" with node 312 of "increased lifespan".

The numeric values of meta-relationship weightings for the sentiment are shown as nodes weightings 330 and edge weightings 340.

The semantic graph 300 with sentiment weightings 330, 340 is used at runtime to detect the correct interpretation of an input sentiment phrase, similar to a word-sense disambiguation (WSD) task.

An example input context is: "Adding ingredient A to drug X strongly increased the lifespan of the patient." versus "The toxicity of drug Y strongly increased when taken in conjunction with drug Z". The concept entities underlined and the sentiment is shown in bold.

The input context is used to activate the graph, using the underlined concept entities to activate the semantic graph 300 at those starting nodes, and the net accumulation of signal on each of the important concepts reflects the sentiment for this phrase.

Bias/Impartiality in Predictive Analytics

As the use of sentiment analysis techniques becomes more prevalent, systematic bias in the evaluation of sentiment can jeopardize the integrity of decisions based on automated sentiment analysis of natural language text. For example, when an article is published about a company or one of its competitors and this article expresses positive or negative opinion about these actors and their future financial performance or about a particular competing product, it is critical that any inherent bias is exposed in order for the article to be treated appropriately. The article may then be excluded from the decision making process or the intensity of the bias may be taken into account when producing the score. The most trustworthy articles are those which do not lean in one or the other direction. Many systems assume that the average sentiment score in a noisy corpus is the neutral one.

Detecting this bias is a complex process that should rely on background information such as previous articles of the same author, but many solutions rely only on a user independent or localized approach that ignores other context. Aggregating this bias in a way that meaningfully expresses the intensity of bias between two entities is addressed by the described method.

The described method aims to produce a balanced representation of bias intensity as distinct from polarity alone. Measuring the impartiality of an author with respect to a given topic is a key enabling factor in assessing the trustworthiness of a data source. When Press A releases a positive news story about Company P, is this from a neutral perspective, or are there other vested interests? When Press A publishes a negative article about a Company Q (a competitor of Company P), can it be trusted? Detecting bias may traditionally result in the content being rejected; however, if it is possible to measure the degree and polarity of that bias, use can be made of the content by taking this degree of bias into account.

The described method provides a technique that not only detects bias, but also quantifies the intensity of the polarity of the relationship between entities. This is extremely useful to NLP systems.

Organizations are usually optimistic in their version of the performance summary and outlook. When projected performance reports are published, they should be examined for bias. Likewise, when competitors or those with vested interest express opinion on the same companies or related topics, a reader should be similarly vigilant. Various news agencies and investment agencies also publish their assessment of an organization's quarterly/annual report and many of them differ from the self-assessment of the organization. In such scenarios, it is very helpful for an investor or observer to be able to arrive at a realistic or weighted average conclusion. To accomplish this, the described method accounts for bias arising out of relationships, ownership, historical transactions, etc., between organizations and agencies and is able to quantify this bias.

For automated Equity Researcher systems, bias detection and analysis is an important task. The degree of confidence in the item of focus is a function of the opinion/semantic and detected bias in the context of those articles. For example, a patent expiry or a change in government regulation can be useful or counterproductive to different entities in an ecosystem depending on their business positions.

In the medical domain, a valuable patent's expiry is a business loss for the owning pharmaceutical company; however, it is a gain for competitors who want to make generics of this formulation, and patients who need it at a cheaper cost. Similarly, a protectionist tariff regime of a government can benefit local producers and hurt importers. The news outlet or agency's perspective can highlight one side over the other or stay neutral and an equity investor needs a tool to get a balanced picture of the event and make a buy/sell/hold decision.

Bias in predictive analysis is an example of a phenomenon for which meta-relationships may be applied and evaluated using a semantic graph using the described method.

Example of Bias Evaluation:

In an example embodiment, a semantic graph may be built from financial domain corpora, using named-entity recognition (NER) data and parse frames over data such as the following:
 a) annual/quarterly reports with numerical details and textual summary and an outlook for short term future;
 b) financial news reports;
 c) financial blogs;
 d) metadata for all of the above, including article author, publication details, etc.

Phrase-level sentiment analysis may be performed on each sentence in the corpus and aggregate scores produced for each pair of entities in the graph that occur in the text. This constitutes the current impartiality landscape in this domain. Edge weightings between entities may be used to describe the degree of polarity (positive and negative) from prior association. In a dynamic processing system, these edge weightings can preserve the latest overall status of this polarity, as a probability of impartiality.

Since bias can be positive, negative or neutral, the feature vector here may include either one or several signed values (−/+) to signify net polarity and individual polarity scores between two entities.

A new article or context may be processed by detecting the same entities and metadata on the input, and performing spreading activation in the graph using the weightings. The signal will traverse the graph according to the strength of the edge weightings, and their polarity will contribute to an overall sum on every node, which is particular to this activation, using the specific starting nodes.

The resulting signal accumulation values on each node are then a reflection of whether or not assertions affecting these entities are trustworthy/impartial, or whether the conclusions and assertions on these entities are trustworthy.

Figure 4A:
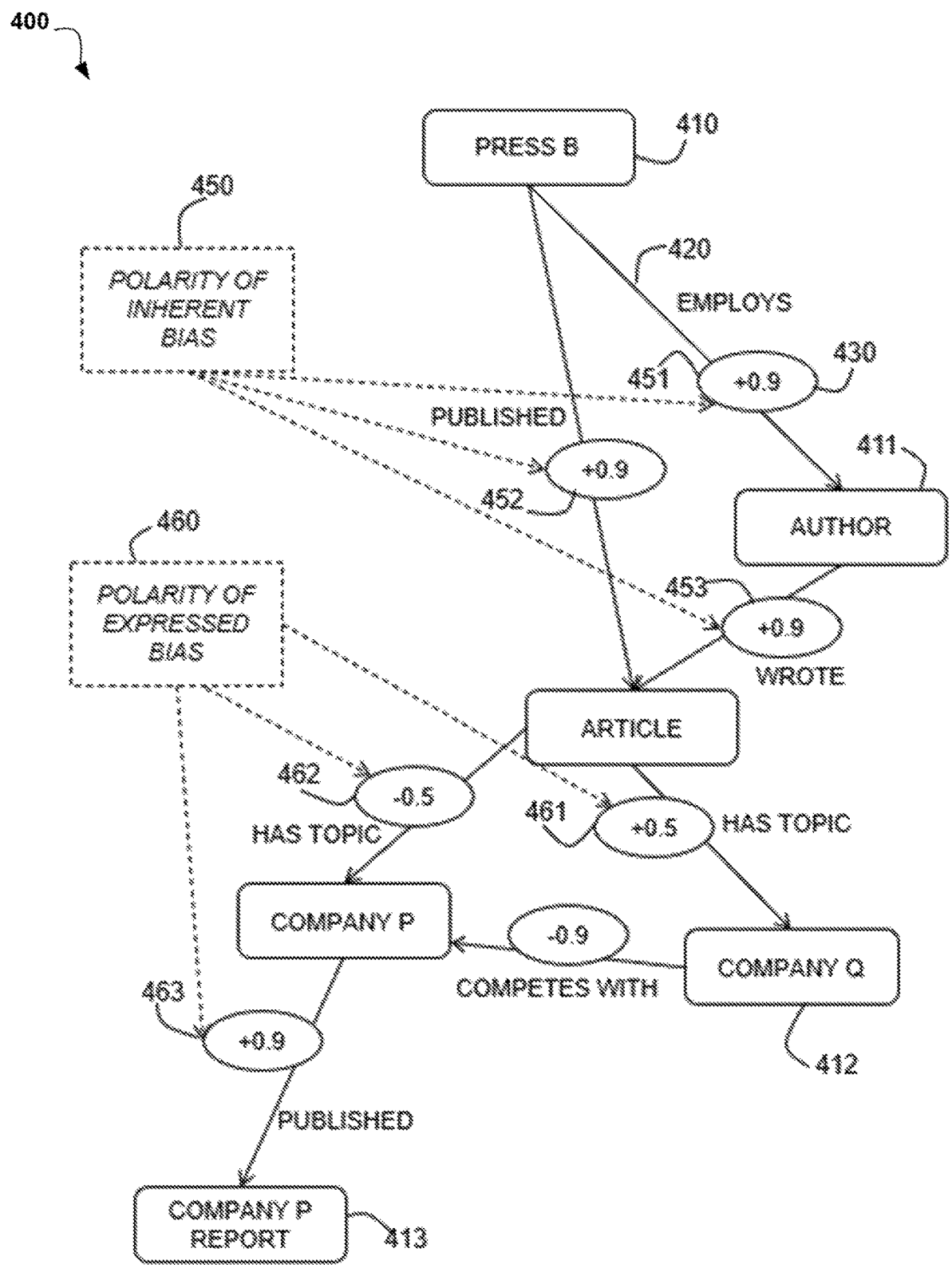
FIGS. 4A and 4B are schematic diagrams illustrating a second example embodiment of a method in accordance with the present invention.
Figure 4B:
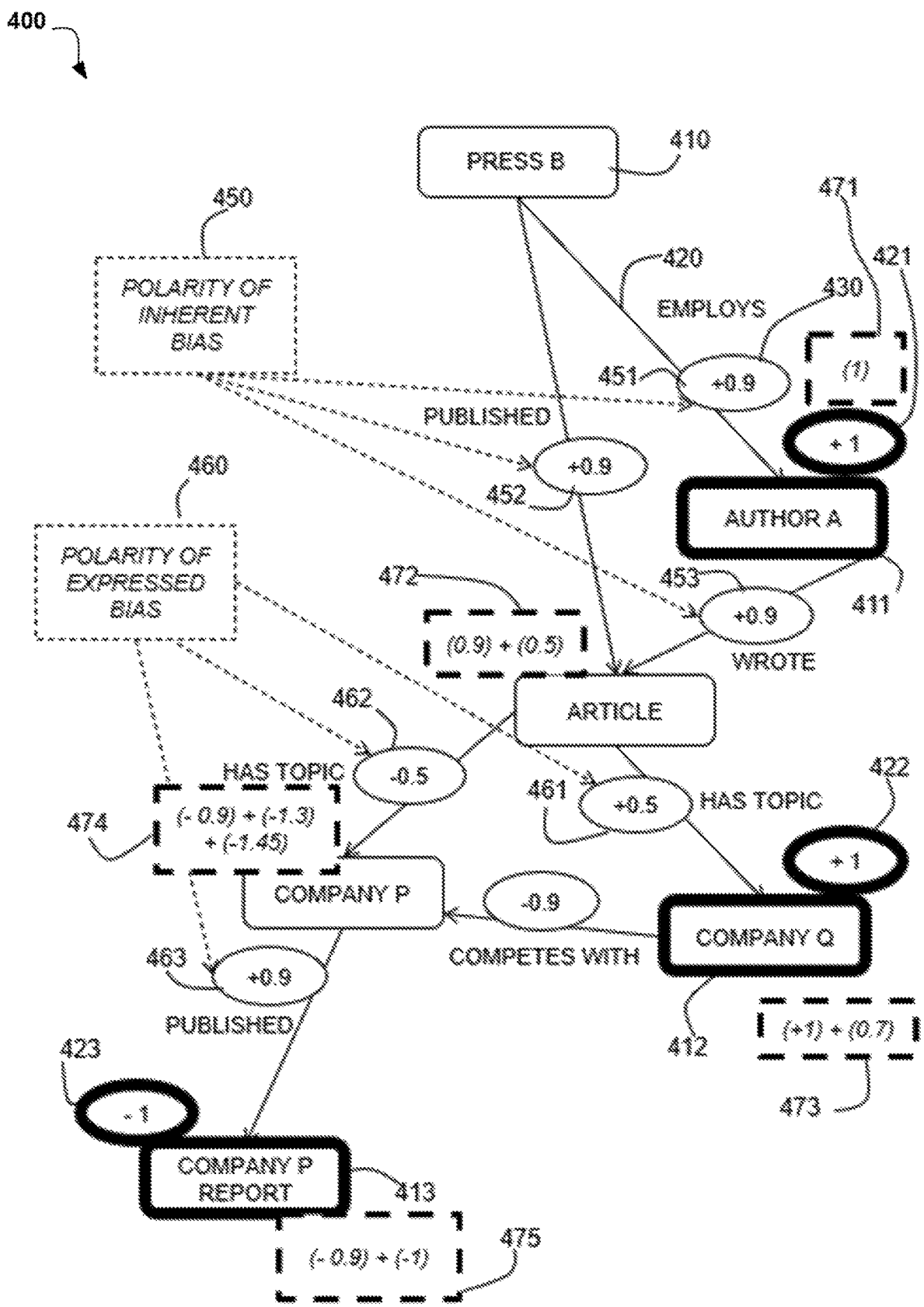

FIGS. 4A and 4B are schematic diagrams of an extract from a semantic graph 400 that illustrates meta-relationship weightings of bias intensity and polarity.

The graph 400 includes nodes 410 of entities with edges 420 for semantic relationships between the entities. The numeric values of meta-relationship weightings 430 are shown on the edges.

The nodes 411, 412, 413 in FIG. 4A reflect the content of a new unseen document where [Author A] 411 is the author and the subjects are [Company P Report] 413 and [Company Q] 412.

The following is a scenario that reflects the values used to seed the activation of the graph 400.

An Article by Author A states the following:

"The new report on financial outlook for Company P is replete with inaccuracies and outlandish predictions that in no way reflect reality. Unlike Company Q, whose CEO has decided to invest well in the latest technology, Company P cannot claim to be going in the right direction, and this report simply looks like an attempt to cover up the cracks in their increasingly poor performance."

Resulting inputs from sentiment analysis of this article above are:

Author A: weighting +1, which is added as node weighting 421;

Company P Report: weighting −1, which is added as node weighting 423; and

Company Q: weighting +1, which is added as node weighting 422.

In the graph 400, prior opinions of Author A are affecting the interpretation of what he/she says. The net outcome suggests that opinions toward certain topics should not be trusted. The polarity of inherent bias 450 is shown in the existing edge weightings 451, 452, 453. The polarity of expressed bias 460 is shown in edge weightings 461, 462, 463.

Certain relationships exhibit inherent bias. A company authored article about the same company has inherent bias, since that company is unlikely to present itself in a negative light. An author employed by a publication has inherent bias toward the general stance and perspectives of that publication, for reasons of job security. A company also has inherent bias with respect to its competitors.

Expressed bias is a reflection of some published instance(s) of sentiment in any polarity toward the topic or entity, such as the example scenario of a published article.

Following an input (for example, the article above) a signal is spread across the weighted edges. Once this process has completed, the activation may be analyzed to see how the signal has accumulated at the input nodes, as well as how other nodes in the graph happen to be weighted, to infer bias between nodes that occurred in the input and any other node(s) in the graph.

Graph activation for the current article calculates spreading activation values 471, 472, 473, 474, 475 and results in the following bias outcomes:

[Author A] on [Company P]=(−0.9)+(−1.3)+(−1.45)= (−3.65) shown as bias outcome 474.

[Author A] on [Company Q]=(+1)+(0.7)=(+1.7) shown as bias outcome 473.

Across a single edge, going into a node, each value is the result of multiplying the value from the starting node with the value on the edge, where the edge was storing prior bias (and polarity) and the node weight is a net accumulated value from the signal moving through the graph.

Some further comments on the above embodiment:

Entities representing authors and publications may have a history of prior articles and press releases, etc. which may have content that can be analyzed for polarity of assertions between concepts in the content. Examples include:

"Company A will go bust", or

"Company B is blazing the trail for AI", or

"financial forecasts for Company A are looking decidedly worse".

Additional features may be extracted from such content using techniques such as tone analysis, sentiment analysis, social network metadata (prior employment, customer history, etc.), as well as the tagging of common themes and topics.

While sentiment and opinion or bias can often be quantified in numeric terms, it is interesting to target the notion of impartiality around statements that appear to be factual and devoid of any inherent polarity, but which are actually questionable based on the ambient relationship between these entities in context. For example, when a company has a contract with Company P and releases articles that refer to Company P's competitors, in ways that can potentially affect their business, it is critically important to be able to detect and call into question the impartiality of such assertions, which the ambient nature of the semantic graph actually encourages.

As new data are released that contain references or metadata associated with entities in the graph, a back end graph monitor may be implemented that keeps track of the degree of bias between pairs of entities that are directly linked. Detecting which edges should be updated can be done in a variety of ways, including:

a) Co-occurring entities in different scopes, such as sentences, noun-phrases, paragraphs, documents or even full publications;

b) Entities linked by dependency parse structure, e.g. parent node→child node, or as arguments of the same verb; and c) Entities that are linked by a particular relationship which has an independent reference in the text, or directly links the domain and range entities in a parse tree, as in predicate (subj, obj).

The formula for polarity that is stored as the edge weighting between two entities may be a function of all prior positive and negative bias, but something as simple as an aggregate sum would work. Statistical techniques that take into account the utility of particular features over others would be helpful in providing a more robust and domain-sensitive weight.

Having identified a set of results for an answer corpus, e.g. through traditional search/IR, equity research focus, etc., it may be appropriate to ignore documents with too much bias or re-weight accordingly.

Bias from one entity toward another is either positive or negative (where neutral bias is not relevant for this scenario). When analysis is available of bias between two entities, such as between an author and a topic, the polarity of the prior bias and the polarity of the document content, different decisions can be made according to the alignment of these data.

An example table demonstrating how this might happen is below, where same sign bias and sentiment should be flagged as either "interesting" or "untrustworthy", and opposing sign bias and sentiment should be re-weighted.

|  | Bias | |
| --- | --- | --- |
| Sentiment | Positive | Negative |
| Positive | 0* | Positive** |
| Negative | Negative | 0 |

For example, if an author with positive bias toward a topic says something positive, it is not so trustworthy, but if they say something negative, it is potentially more noteworthy than the perspective of an unbiased author (and vice versa for the reverse in polarity).

Therefore in the above table:
0—Should be considered untrustworthy and can be ignored;
*Positive/Negative—Unexpected and therefore of additional value; and
Neutral values may be considered equivalent.

AlchemyLanguage (a trademark of International Business Machines Corporation) is a collection of application programming interfaces that offer text analysis through NLP. Further implementation may take the sentiment analysis of opinion of AlchemyLanguage toward entities.

Query Expansion Using Information Retrieval Statistics

Aside from hard coded weightings for semantic categories and entities that may be more or less relevant to the content of a semantic graph, there are many other ways in which semantic relevance can be encoded as a spreading signal in a semantic graph. An embodiment of the described method may be provided as an automated configuration of spreading activation for semantic relevance using information retrieval (IR) frequency from domain specific corpora to weight graph nodes and links.

Another way of viewing semantic relevance is in the strength of association with a particular body of content. Re-weighting a semantic graph by the inverse of the strength of association is therefore going to promote those concepts that are less common. This can be very helpful in adapting a semantic graph for a new domain. In the initial domain, which was used to construct the original semantic network, the default weights for activation may be sufficient. However, there is an inherent bias built into this network as to the relevance of particular concepts. Even using traditional IR statistics such as term frequency and co-occurrence frequency can help to adapt a spreading signal in this graph, in order to produce more meaningful output in new domains.

Example of Additional Semantic Evaluation:

In an example embodiment, an existing semantic graph may be used; for example, a UMLS—medical domain graph, or DBPedia—open domain graph.

A corpus of natural language text in a new domain may be used as an additional resource for the meta-relationship, and corpus frequencies of entities and relationships in this domain may be gathered.

Values may be aggregated and stored in the semantic graph as weightings for the meta-relationship for nodes and edges:
a) Node frequencies (Fn) reflect generality of a term and as such the reciprocal 1/Fn will be used;
b) Edge frequencies (Fe) are directly proportional to the relevance of a term and the value Fe is used;
c) Values scaled down to fit between 0 and 1 or 0.5 and 1 is very common in spreading activation for recursive diminishing of a propagating a signal;
d) Other variations on above would include using tf/idf scores for nodes and edges.

Given an input context, instances of entities may be recognized in the semantic graph, the graph activated at those points, and spreading activation performed in the context of a particular NLP task, such as word sense disambiguation (WSD), word sense induction (WSI) or query expansion.

The output is much more relevant to the domain than it would otherwise be.

Query Expansion Example:

The process of query expansion may be considered to be to understand the context of an input phrase or query and to find alternative or additional phrases that should help to find the correct document(s) for the original query. An example is "Where is Company A's office in Ireland?" Refining "Ireland" to "Cork", "Dublin" and "Galway" where Company A has offices, would potentially improve the chances of finding the right answer. Query expansion typically focuses on aspects of the input and attempts to extrapolate so as to improve the likelihood of a match.

The effect of applying this technique in query expansion may be demonstrated. Centre nodes may be query expansion candidates, and surrounding nodes may be from the input context. After configuring spreading activation to take information retrieval statistics into account, the relevance scores of more general concepts becomes low enough to exclude them as irrelevant to the context. The knock on effect of this is that the rank of candidates for query expansion also changes. When rank is by number of mutually related relevant inputs, a new top-ranked query expansion candidate may be obtained.

An initial attempt to obtain an additional helpful query term for the inputs "public record", "law", "information", "political subdivision", etc. may give a best candidate of central node as "law enforcement agency". Following the weighting of the graph according to the frequency of nodes in the domain corpus, several of the original inputs may no longer be deemed as suitable inputs, and the term "confidential information" may be proposed as the central node instead. Given that the original context was in the domain of "data privacy", this is a big improvement.

Automated Risk Assessment

The field of automated risk assessment relies predominantly on keyword based approaches where there is a direct link between a given keyword and a particular level of risk exposure. Machine learning techniques are typically used to give a more robust recognition of outcomes based on those keywords and their associated risk factors. Approaches that can infer risk exposure and quantify it using knowledge that may not be directly present in the context will be of significant additional value to existing techniques.

The degree or intensity of exposure to risk is something that can be quantified with respect to particular risk factors, in a similar way to sentiment analysis or geo-spatial inference. A further embodiment of the method that leverages the same technique to perform risk assessment is anticipated. Existing solutions to this problem using NLP techniques involve linking particular keywords or phrases to risk, similar to lexicon based sentiment analysis. A system that can infer risk exposure in a more ambient fashion would be extremely valuable in producing an intensity measure for risk exposure in context.

Taking one example from the medical domain, the specifics of the Framingham risk assessment tool for estimating a patient's 10-year risk of developing cardiovascular disease may be encoded into the graph structure. As spreading activation is performed in the graph, the intensity of signal propagation on each of the relevant named entities becomes directly proportional to the level of risk to the patient.

Geo-Spatial Inference

In the same way that bias can be quantified according to the intensity of historic sentiment polarity, the relevance of an entity or topic to a list of geographic places can be evaluated according to historic association and geographic distance. Existing methods for geospatial inference are limited to direct mentions in text, but when multiple locations exist in text, a method that can determine the relevance by universal association in a domain corpus is much more valuable.

A feature vector for the meta-relationship weightings for geographic relevance may include a combination of the following sample features:
   a) a normalized geographic distance between two entities;
   b) a semantic association relevance (e.g. the weight from the original spreading activation implementation);
   c) an alternative to b) where only geo-spatial semantic categories are traversed and used for weight accumulation.

Take, for example, a law in a California statute that uses much vocabulary inherent to the CA legislature, but which cites laws in other states or mentions particular places by name that are not in California, for the purposes of the law in question (such as customer data transfer between US and EU based companies). An ambient technique that can infer relevance of California over those locations explicitly mentioned in the text would be extremely useful for legal domain NLP tasks.

Figure 5:
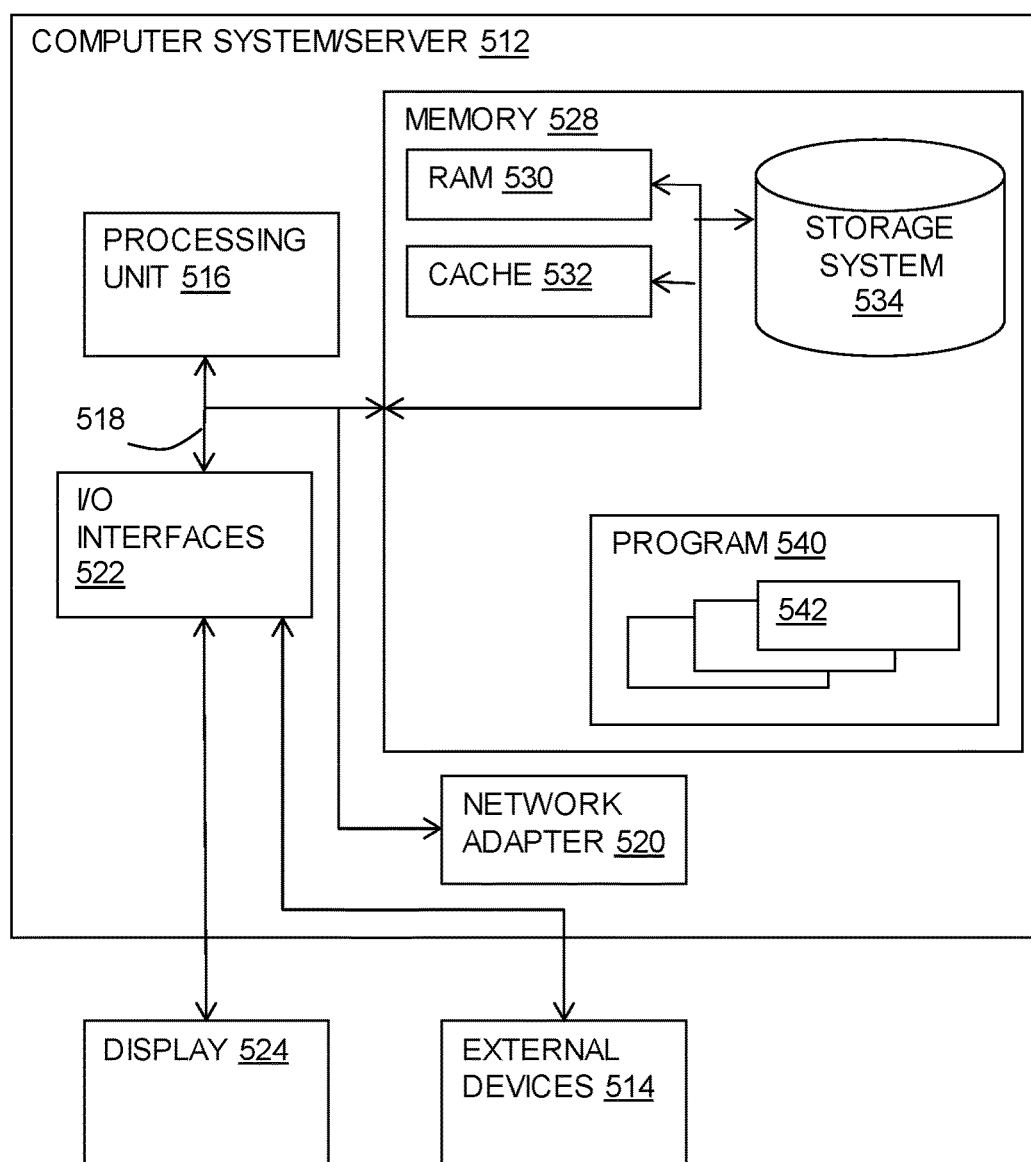
FIG. 5 is a block diagram of an embodiment of a computer system or cloud server in which the present invention may be implemented.

Referring now to FIG. 5, a schematic of an example of a system 500 in the form of a computer system or server is shown.

A computer system or server 512 may be operational with numerous other general purpose or special purpose computing system environments or configurations. Examples of well-known computing systems, environments, and/or configurations that may be suitable for use with computer system/server 512 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 512 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 512 may be practiced in distributed cloud computing environments where tasks are performed by remote processing devices that are linked through a communications network. In a distributed cloud computing environment, program modules may be located in both local and remote computer system storage media including memory storage devices.

In FIG. 5, a computer system/server 512 is shown in the form of a general-purpose computing device. The components of the computer system/server 512 may include, but are not limited to, one or more processors or processing units 516, a system memory 528, and a bus 518 that couples various system components including system memory 528 to processor 516.

Bus 518 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 512 typically includes a variety of computer system readable media. Such media may be any available media that are accessible by computer system/server 512, and they include both volatile and non-volatile media, removable and non-removable media.

System memory 528 can include computer system readable media in the form of volatile memory, such as random access memory (RAM) 530 and/or cache memory 532. Computer system/server 512 may further include other removable/non-removable, volatile/non-volatile computer system storage media. By way of example only, storage system 534 can be provided for reading from and writing to non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 518 by one or more data media interfaces. As will be further depicted and described below, memory 528 may include at least one program product having a set (e.g., at least one) of program modules that are configured to carry out the functions of embodiments of the invention.

Program/utility 540, having a set (at least one) of program modules 542, may be stored in memory 528 as well as, by way of example and not limitation, an operating system, one or more application programs, other program modules, and program data. Each of the operating system, one or more application programs, other program modules, and program data or some combination thereof, may include an implementation of a networking environment. Program modules 542 generally carry out the functions and/or methodologies of embodiments of the invention as described herein.

Computer system/server 512 may also communicate with one or more external devices 514 such as a keyboard, a pointing device, a display 524, etc.; one or more devices that enable a user to interact with computer system/server 512; and/or any devices (e.g., network card, modem, etc.) that enable computer system/server 512 to communicate with one or more other computing devices. Such communication can occur via Input/Output (I/O) interfaces 522. Still yet, computer system/server 512 can communicate with one or more networks such as a local area network (LAN), a general wide area network (WAN), and/or a public network (e.g., the Internet) via network adapter 520. As depicted, network adapter 520 communicates with the other components of computer system/server 512 via bus 518. It should be understood that although not shown, other hardware and/or software components could be used in conjunction with computer system/server 512. Examples include, but are not limited to: microcode, device drivers, redundant processing units, external disk drive arrays, RAID systems, tape drives, data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Cloud Computing

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
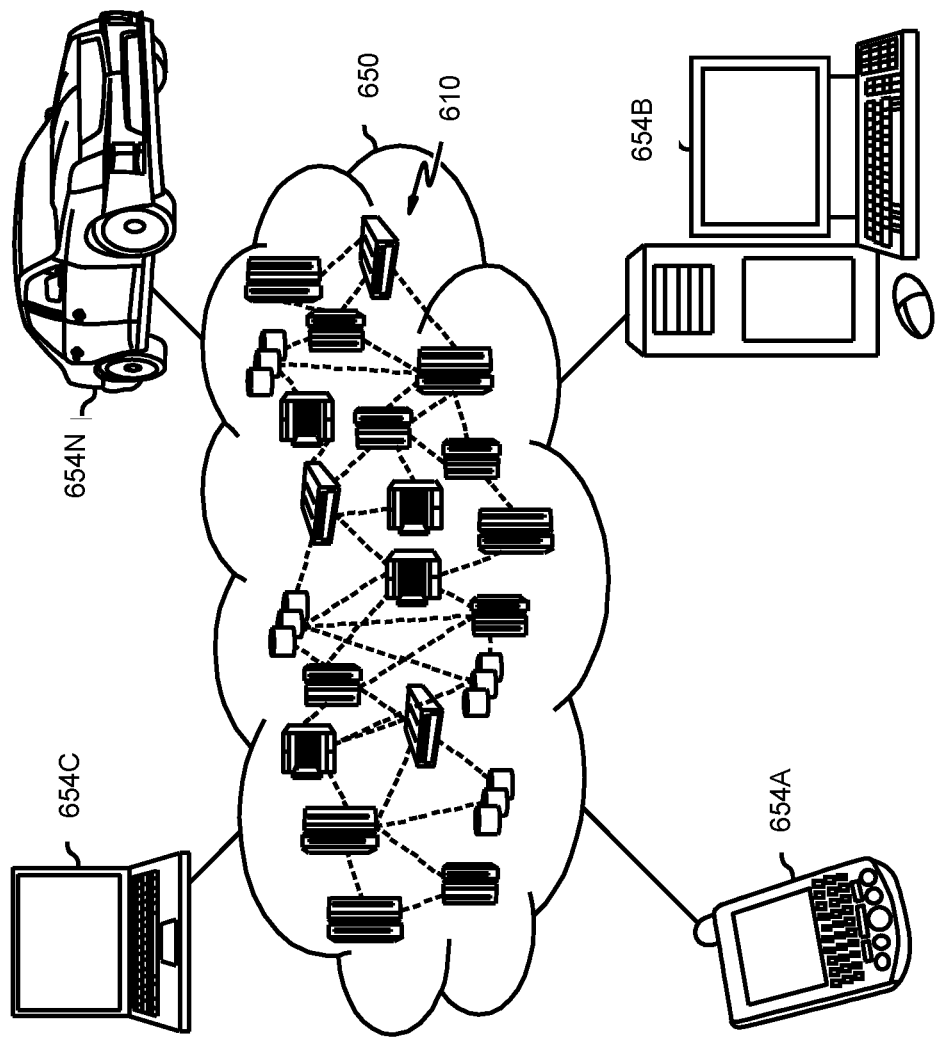
FIG. 6 is a schematic diagram of a cloud computing environment in which the present invention may be implemented.

Referring now to FIG. 6, an illustrative cloud computing environment 650 is depicted. As shown, cloud computing environment 650 includes one or more cloud computing nodes 610 with which local computing devices used by cloud consumers, such as, personal digital assistant (PDA) or cellular telephone 654A, desktop computer 654B, laptop computer 654C, and/or automobile computer system 654N may communicate. Nodes 610 may communicate with one another. They may be grouped (not shown) physically or virtually, in one or more networks, such as Private, Community, Public, or Hybrid clouds as described hereinabove, or a combination thereof. This allows cloud computing environment 650 to offer infrastructure, platforms and/or software as services for which a cloud consumer does not need to maintain resources on a local computing device. It is understood that the types of computing devices 654A-N shown in FIG. 6 are intended to be illustrative only and that computing nodes 610 and cloud computing environment 650 can communicate with any type of computerized device over any type of network and/or network addressable connection (e.g., using a web browser).

Figure 7:
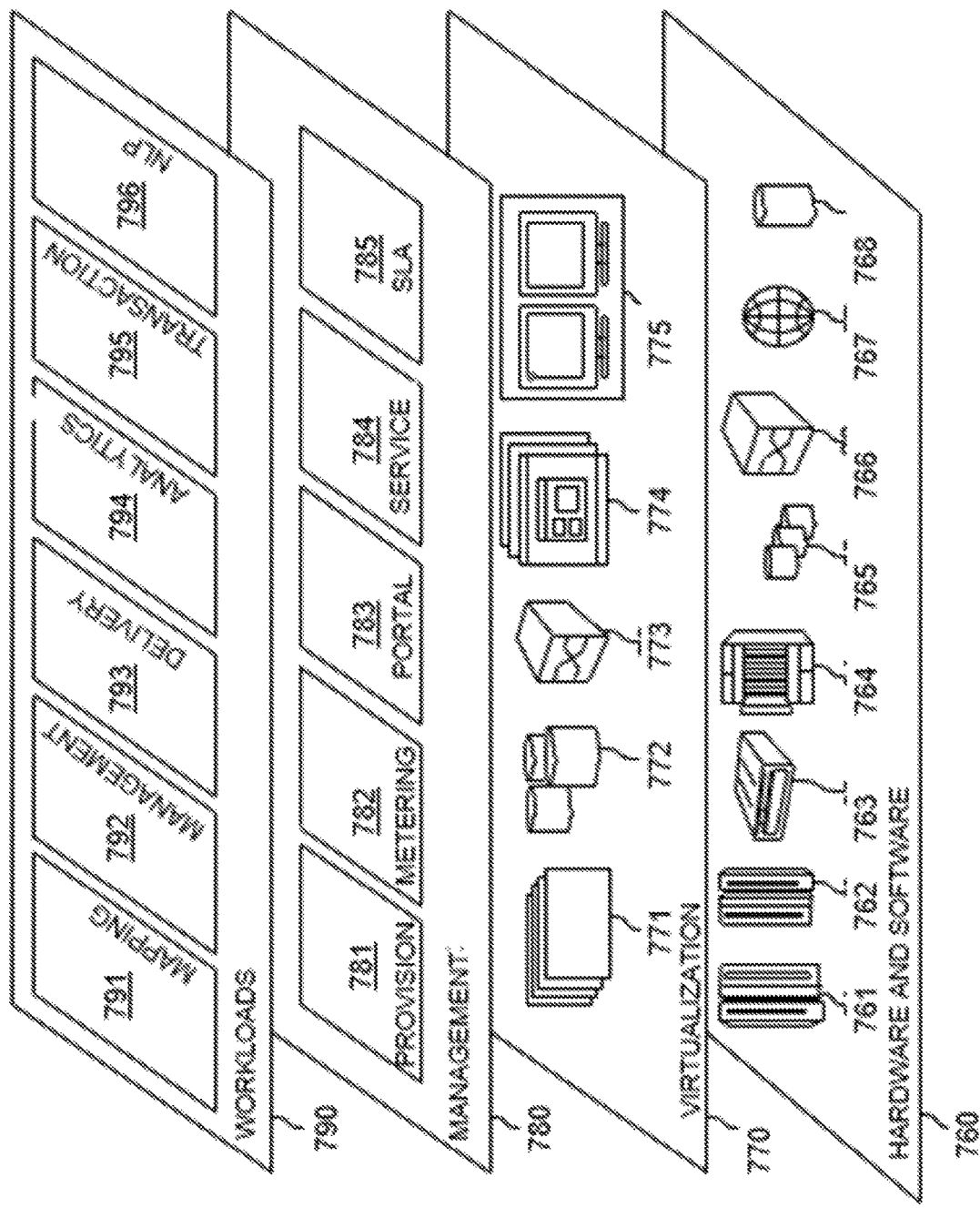
FIG. 7 is a diagram of abstraction model layers of a cloud computing environment in which the present invention may be implemented.

Referring now to FIG. 7, a set of functional abstraction layers provided by cloud computing environment 650 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 760 includes hardware and software components. Examples of hardware components include: mainframes 761; RISC (Reduced Instruction Set Computer) architecture based servers 762; servers 763; blade servers 764; storage devices 765; and networks and networking components 766. In some embodiments, software components include network application server software 767 and database software 768.

Virtualization layer 770 provides an abstraction layer from which the following examples of virtual entities may be provided: virtual servers 771; virtual storage 772; virtual networks 773, including virtual private networks; virtual applications and operating systems 774; and virtual clients 775.

In one example, management layer 780 may provide the functions described below. Resource provisioning 781 provides dynamic procurement of computing resources and other resources that are utilized to perform tasks within the cloud computing environment. Metering and Pricing 782 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 783 provides access to the cloud computing environment for consumers and system administrators. Service level management 784 provides cloud computing resource allocation and management such that required service levels are met. Service Level Agreement (SLA) planning and fulfillment 785 provide pre-arrangement for, and procurement of, cloud computing resources for which a future requirement is anticipated in accordance with an SLA.

Workloads layer 790 provides examples of functionality for which the cloud computing environment may be utilized. Examples of workloads and functions which may be provided from this layer include: mapping and navigation 791; software development and lifecycle management 792; virtual classroom education delivery 793; data analytics processing 794; transaction processing 795; and adaptive evaluation of meta-relationships in semantic graphs using natural language processing 796.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Improvements and modifications can be made to the foregoing without departing from the scope of the present invention.

What is claimed is:

1. A computer system for adaptive evaluation of meta-relationships in semantic graphs, the computer system comprising:
a processor and a memory configured to provide computer program instructions to the processor to execute a method comprising:
deriving a semantic graph from a natural language source based on a knowledge base in which concepts in a form of graph nodes are linked by semantic relationships in a form of graph edges;
encoding in metadata of the edges and nodes of the semantic graph, weightings as feature vectors for measuring a meta-relationship, wherein the meta-relationship applies to the concepts of the semantic graph and is independent of the semantic relationship defined by the edges of the semantic graph, wherein the feature vectors comprise an intensity of the meta-relationship and a confidence score of the intensity, and wherein the intensity uses runtime inputs for the nodes;
carrying out a graph activation for an input context relating to one or more concepts of the semantic graph, wherein the weightings are applied to a spreading activation signal through the semantic graph to produce a measure of the meta-relationship for a sub-set of concepts of the semantic graph;
scoring the edges and nodes of the semantic graph in response to the graph activation;
seeding the graph with seed weightings for measures of the meta-relationship obtained from a set of resources independent of the knowledge base on which the semantic graph is based; and
in response to additions to the set of resources independent of the knowledge base on which the semantic graph is based updating the seed weightings.

2. The computer system of claim 1, wherein carrying out the graph activation for the input context relating to one or more concepts of the semantic graph further comprises:
discovering instances of concepts in the input context; and
activating nodes corresponding to the concepts in the semantic graph, traversing a signal outward to adjacent nodes activating the adjacent nodes in turn whilst applying the weightings to the signal, and determining one or more focus nodes with a highest resultant activation signal.

3. The computer system of claim 2, further comprising outputting a resultant activated portion of the semantic graph reflecting a measurement of the meta-relationship in the input context.

4. The computer system of claim 3, further comprising outputting an activated sub-graph where the activation weightings on nodes and edges represent the measurement of the meta-relationship.

5. The computer system of claim 1, further comprising:
in response to additions to the input context, updating the seed weightings.

6. The computer system of claim 1, wherein the weightings are feature vectors and the method further comprises calculating the feature vectors in response to runtime inputs for the nodes for instances of concepts of the input context.

7. The computer system of claim 6, wherein the feature vectors include relevance factors to be applied to the runtime inputs for the nodes.

8. The computer system of claim 6, wherein the feature vectors include semantic and/or lexical features for instances of concepts in the input context in addition to the meta-relationship.

9. The computer system of claim 6, wherein the feature vectors define confidence scores for the weightings.

10. The computer system of claim 1, wherein the meta-relationship relates to a phenomenon in a form of one of a group consisting of:
sentiment analysis, bias evaluation, bias in predictive analysis, query expansion using information retrieval, risk assessment, geo-spatial inference, and suitability of treatment, use or handling including clinical trial matching.

11. A computer program product for adaptive evaluation of meta-relationships in semantic graphs, the computer program product comprising a computer readable storage medium having program instructions embodied therewith, the program instructions executable by a processor to cause the processor to:

deriving a semantic graph from a natural language source based on a knowledge base in which concepts in a form of graph nodes are linked by semantic relationships in a form of graph edges;

encode in metadata of the edges and nodes of the semantic graph, weightings as feature vectors for measuring a meta-relationship, wherein the meta-relationship applies to the concepts of the semantic graph and is independent of the semantic relationship defined by the edges of the semantic graph, wherein the feature vectors comprise an intensity of the meta-relationship and a confidence score of the intensity, and wherein the intensity uses runtime inputs for the nodes;

carry out a graph activation for an input context relating to one or more concepts of the semantic graph, wherein the weightings are applied to a spreading activation signal through the semantic graph to produce a measure of the meta-relationship for a sub-set of concepts of the semantic graph;

score the edges and nodes of the semantic graph in response to the graph activation;

seed the graph with seed weightings for measures of the meta-relationship obtained from a set of resources independent of the knowledge base on which the semantic graph is based; and in response to additions to the set of resources independent of the knowledge base on which the semantic graph is based, update the seed weightings.

* * * * *